United States Patent [19]

Michel et al.

[11] Patent Number: 5,370,629
[45] Date of Patent: Dec. 6, 1994

[54] INJECTION DEVICE

[75] Inventors: Peter Michel, Burgdorf; Fritz Kirchhofer, Sumiswald, both of Switzerland

[73] Assignee: Medimpex Ets., Balzers, Liechtenstein

[21] Appl. No.: 133,108

[22] PCT Filed: Feb. 12, 1993

[86] PCT No.: PCT/CH93/00037

§ 371 Date: Oct. 13, 1993

§ 102(e) Date: Oct. 13, 1993

[87] PCT Pub. No.: WO93/16740

PCT Pub. Date: Sep. 2, 1993

[30] Foreign Application Priority Data

Feb. 21, 1992 [CH] Switzerland ............ 0053492-3

[51] Int. Cl.$^5$ ............................................ A61M 5/00
[52] U.S. Cl. ...................................... 604/207; 604/232
[58] Field of Search ............... 604/207, 208, 209, 210, 604/211, 218, 232, 187

[56] References Cited

U.S. PATENT DOCUMENTS

| | | | |
|---|---|---|---|
| 4,973,318 | 11/1990 | Holm et al. | 604/208 |
| 5,017,190 | 5/1991 | Simon et al. | 604/207 |
| 5,292,318 | 3/1994 | Haber et al. | 604/207 X |
| 5,295,976 | 3/1994 | Harris | 604/211 |
| 5,304,152 | 4/1994 | Sams | 604/207 |

Primary Examiner—John D. Yasko
Attorney, Agent, or Firm—Walter C. Farley

[57] ABSTRACT

The invention concerns an injection device (1) receiving in exchangeable manner an ampoule (4) with a plunger (5) and an injection needle (6). It further comprises an actuation means (7) essentially consisting of an operating head (8), a drive element (11), a guide element (24) and an output member (9, 19) preferably in the form of a rod (9) and flange (19). The output member is non-rotatably affixed to the guide element (11) itself rigidly mounted inside the device (1) and seated by its own thread in an internal thread (27) of the drive element (11) which can be displaced axially and into rotation by the manual operating head (8). When rotating the operating head (8), the output member (9, 19) is advanced and in the process forces forward the plunger (5), the result being injection. The stationary guide element (24) of the disclosed device is located axially ahead of the axially displaceable drive element (11). Accordingly the length of the actuation system (7) is shorter than in state-of-the-art injection devices, whereby a larger maximum dose can be injected with a device (1) of the same length. The device (1) is applicable in medicine.

8 Claims, 4 Drawing Sheets

INJECTION DEVICE

The invention concerns an injection device defined in the preamble of claim 1.

An injection device of this kind (hereafter frequently shortened to "device") is known from WO 87/02895.

The known injection device is used to inject specific, selected quantities of liquid from a plunger-fitted ampoule. It comprises a manually actuated system including an output member preferably in the form of flanged rod displaceable in the direction of plunger advance and an operational head which can be moved both axially and rotationally. A drive element displaceably supporting the output member can be moved along the plunger advance from a rest position into an end position and back into the rest position. When the drive element is in its rest position, the output member, then a distance from the plunger, can be displaced in the direction of advance over a path corresponding to the plunger stroke required for the particular quantity of liquid to be injected without impacting the plunger. The plunger stroke is determined by the rotation of the operational head. A detent mechanism emitting a slight acoustic signal when passing each detent allows the patient to count these signals and thus to ascertain the magnitude of the new injection dose. While the drive element is advanced from the rest position into the end position, the output member impacts the plunger which it then displaces along the pre-selected plunger stroke. A spring keeps the drive element in its rest position and loads it when it is moved into the end position.

In practical application, this injector is not entirely satisfactory for the following reasons.

The dimensions of the injector are approximately those of a fountain pen because it must be worn constantly by the patients who may need an injection at any time. However, the relation between the length of the actuation system and the maximum injected dose of this known injector falls short because the maximum injection dose supplied by this injector is insufficient for some patients. On the other hand, ampoule size and concentrations of the injection solutions in use have long been set and changing them would meet with much resistance from drug makers. Accordingly, an injector of the given total length is desired which would allow injection of larger maximum doses.

Accordingly, an object of the invention is to create an injection device of approximately the same size as the known injector but permitting administrating of larger injection doses.

This object is achieved by the features of the characterizing part of claim 1; the further claims relate to advantageous embodiments.

The invention is illustrated in the drawings.

The same parts are denoted by the same references in the drawings.

Figure 1:
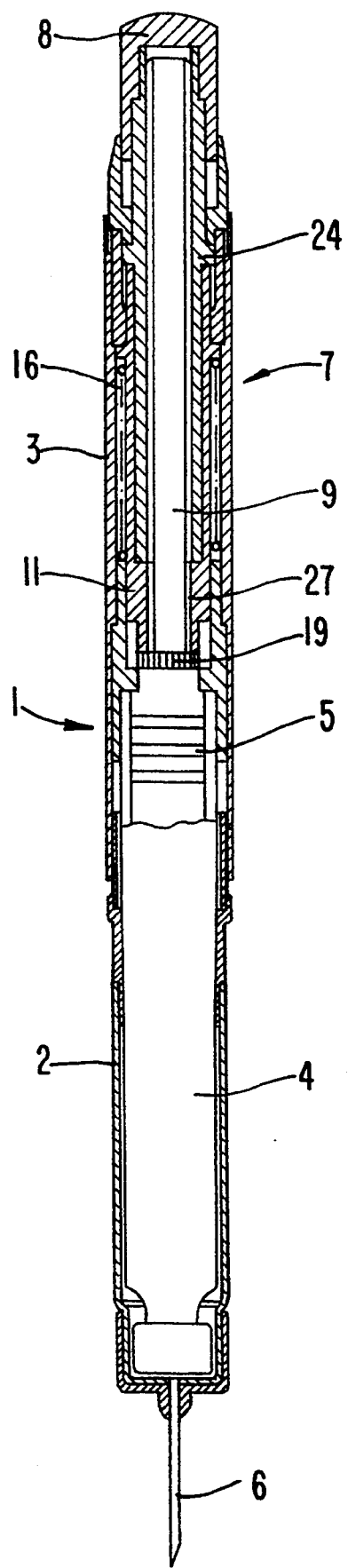
FIG. 1 is a longitudinal section of an injector of the state of the art.
Figure 2:
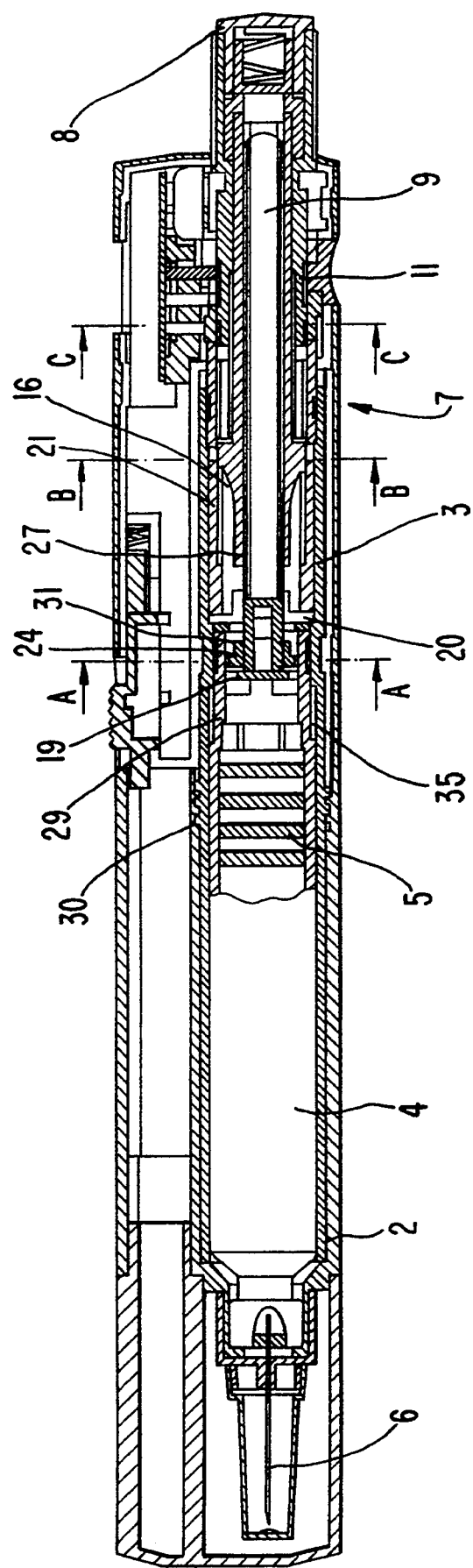
FIG. 2 is a longitudinal section of the injection device of the invention.
Figure 4:
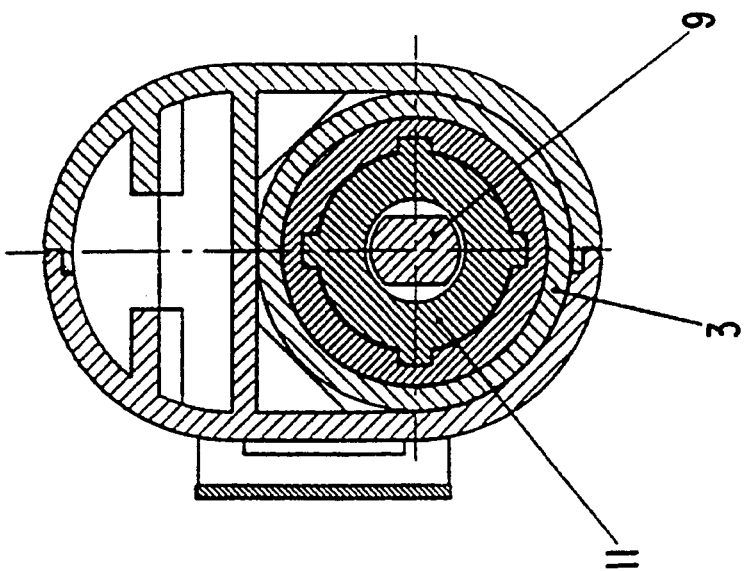
FIG. 4 is the cross-section B—B of the device of FIG. 2.
Figure 3:
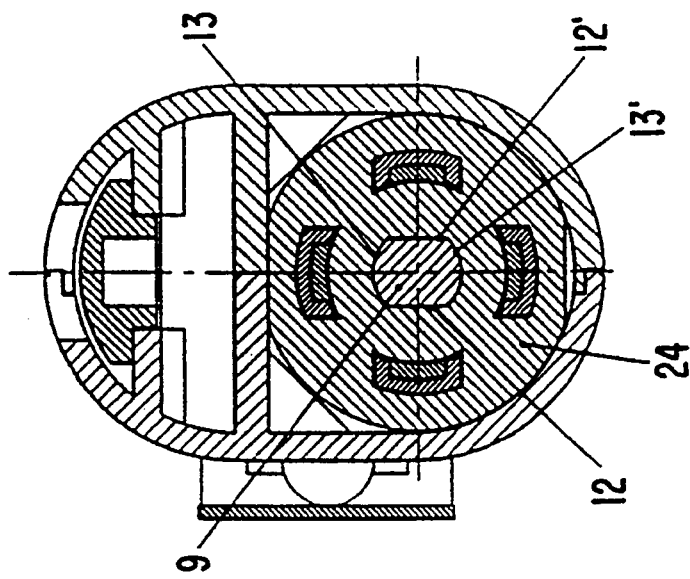
FIG. 3 is the cross-section A—A of the device of FIG. 2.
Figure 6:
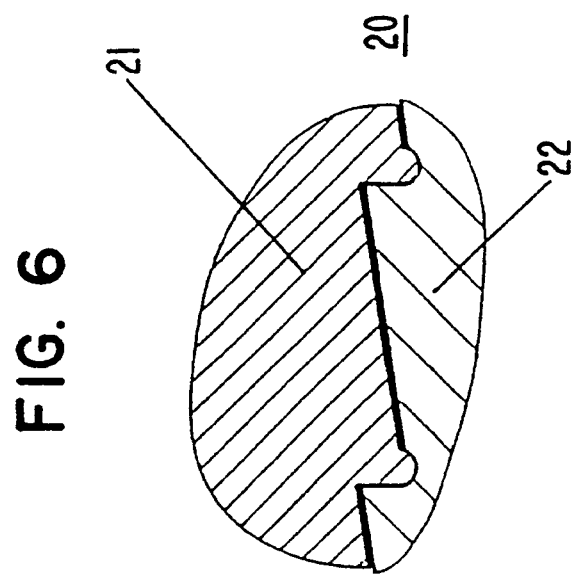
FIG. 6 is a geometric development along the direction D—D of FIG. 2.
Figure 5:
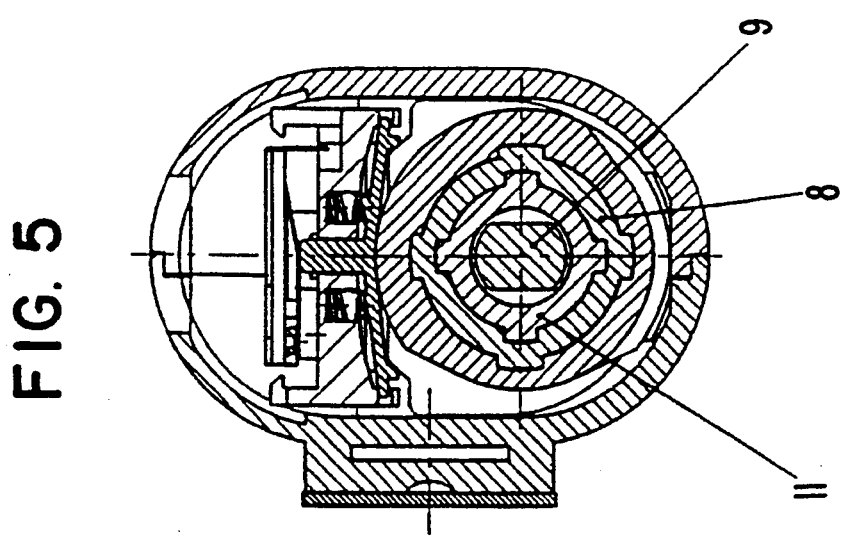
FIG. 5 is the cross-section C—C of the device of FIG. 2.

A known injector 1 as shown in FIG. 1 (and in FIGS. 1 through 7 of WO 87/02895) is described in detail in the following. At its front part 2 it comprises a replaceable ampoule 4 with a plunger 5 to drive the substance to be injected through an injection needle 6. At its rear portion 3 it includes a manually operated, tubular actuation system 7 fitted with an operating head 8, an output member preferably in the form of a rod 9 with a flange 19, a guide element 24 and a drive element 11.

While evincing an overall circular cross-section, the rod 9 has planar surfaces at both sides and is threaded on the circular parts. It is seated by this thread in an internal thread 27 of drive element 11 which is non-rotatably affixed to injector 1. Together with the entire actuation system 7, the drive element 11 can be moved against the force of a spring 16 from a rest position into an end position by axially driving operating head 8 and transmitting this motion through guide element 24. Rod 9 also participates in this displacement. In the process, a flange 19 at the front of the rod 9 forces forward plunger 5 of ampoule 4 and thus implements the injection.

Furthermore, rod 9 is mounted non-rotatably but axially displaceably in the guide element 24 which has the same cross-section, at least in part and up to sliding tolerances as rod 9. In turn, guide element 24 is non-rotatably connected to operating head 8. Operating head 8, guide element 24 and rod 9 can be rotated only in the rest position of actuation system 7. In that case, rod 9 rotates in the internal thread 27 of drive element 11 non-rotatably affixed to injector 1 and thereby moves forward, or when the direction of rotation of operating head 8 is reversed, moves backward.

If an injection was carried out previously, the quantity of substance to be used in the following injection can be ascertained by advancing rod 9 by a given length by rotating operating head 8. This adjustment is limited in such manner by stops in the actuation system 7 that flange 19 cannot touch plunger 5 of ampoule 4 when the quantity to be injected is being set.

In order to determine the adjustment length corresponding to the quantity to be injected, the described injector 1 will emit a clear acoustic signal upon each 90° turn of the operating head, this signal emanating from a rotary detent located between rotating guide element 24 and the drive non-rotatable guide element in injector, as a result of which the patient can adjust the quantity to be injected by counting the acoustic detent signals.

In the known injector 1, the non-rotatable drive element 11 in said injector is located ahead of guide element 24. Rod 9 is supported solely in rotationally displaceable manner in the internal thread 27 of drive element 11 and this rod 9 must be advanced when transition takes place from the rest position to the end position. Therefore, the known injector requires that during the transition from rest position to end position, drive element 11 also shall be advanced.

FIGS. 2 through 6 show the injection device of the invention. It also comprises a front part 2 receiving an ampoule 4 with a plunger 5 and an injection needle 6. The front part 2 and a rear part 3 are connected by a coarse thread 30 by which ampoule 4 is easily replaced. An actuation system 7 is in rear part 3 and consists essentially of an operating head 8, a drive element 11, a guide element 24 and an output member 9, 19 composed of a rod 9 and flange 19. The rod 9 has two planar surfaces 12, 12' at its longitudinal sides and two circular areas 13, 13' with threaded portions. The ampoule 4 furthermore may be replaced by another receptacle with plunger 5.

Drive element 11 is tubular and non-rotatably joined to operating head 8. Rod 9 is inside this drive element 11 which comprises at its front end an internal thread 27 engaging the threads of rod 9. Rod 9 passes through the drive element 11 and through guide element 24. Guide element 24 is rigidly affixed to rear part 3 of the device and therefore is unable to move either axially or rotationally. The aperture of guide element 24 passing the rod 9 has the same diameter, except as enlarged for tolerances, as rod 9, that is, two planar and two circular peripheral parts, as a result of which rod 9 can only move axially, not rotationally, through the aperture of guide element 24.

Operating head 8 is actuated manually and is able to move axially, and for a rest position of actuation system 7 also rotationally. If it is depressed axially, then it will displace the drive element 11 as far as an end position determined by a stop 31 for instance of the drive element 11 at guide element 24 which is solidly affixed to the device rear part 3 to prevent axial displacements.

Rod 9 is seated in internal thread 27 of drive element 11 and thereby undergoes said axial displacement. Nor is this axial displacement hampered by guide element 24 connected non-rotatably and axially rigidly to rear part 3, because the aperture of guide element 24 has the same cross-section as rod 9 and they move axially inside each other while being non-rotatable.

This axial displacement takes place against the force of a spring 16 housed in a clearance between drive element 11 carrying out the axial displacement and a sleeve part 21 of a rotary detent 20. The first spring 16 returns the actuation system 7 into the rest position.

When operating head 8 is rotated to set the next injection dose, then drive element 11 rotates concurrently. However, this rotation cannot be transmitted to rod 9 which rests non-rotatably in guide element 24. Because of the rotating internal thread 27 of the guide element 11, the rod is non-rotatably driven forward (or, if the direction of rotation at the operating head is reversed, backward) by its threaded segments at circular areas 13, 13', and thereby flange 19 is moved to that position which is required by the injection dose to be delivered next, that is, the distance between flange 19 and plunger 5 is correspondingly decreased.

Thereupon, depressing operating head 8 advances actuation system 7 from its rest position into the end position. In the process, flange 19 impacts plunger 5 and drives it along the adjusted plunger stroke, whereby the pre-set volume of injection liquid is expelled through injection needle 6. The path of flange 19 from the rest to the end position of the actuation system 7 always is the same and corresponds to the constant distance by which the flange 19 was apart from the plunger 5 before the injection dose was set.

A rotary detent 20 is located between the non-rotatable and rotational parts of the injection device. It is shown in partial view D in a geometrically developed manner in FIG. 6 for the neutral diameter. The ampoule-holder 29 with its projections 22 passing through guide elements 24 cooperates with sleeve part 21 to form a detent. Both their touching ends are illustratively serrate (FIG. 6) and thus form rotary detent 20. Sleeve part 21 is pressed by first spring 16 touching drive element 11 against the projections of ampoule holder 29, as a result of which rotary detent 20 easily moves in one direction of rotation while not at all in the other.

That direction of rotation by which operating head 8 moves output member 9, 19 into the position corresponding to the next injection dose is the low-drag direction of rotation. If when changing an ampoule 4 rod 9 must be rotated back, then, when removing the old ampoule 4, the ampoule holder 29 is advanced by a spring 35 seated between rear part 3 and ampoule holder 29, as a result of which rotary detent 20 is released in both directions of rotation and therefore rod 9 can easily be rotated back into the initial position using operating head 8.

In the injection device of the invention stationary guide element 24 is in front of the drive element 11. When in transit from the rest position into the end position, only the drive element is displaced axially, forward guide element 24 being unaffected by this displacement. Consequently the overall actuation system 7 is now shorter than in the prior art, and for the same overall length of injector of the prior art and injection device of the invention, the displaceable length between the rest position and the end position for flange 19 joined to rod 9 can be made larger for the device of the invention. Accordingly the injection device of the invention meets the objective of this invention, namely to provide an adjustable injection dose which is larger than in the previously known art.

We claim:

1. Injection device to inject particular, selectable quantities of liquid from a liquid receptacle (4), in particular an ampoule (4), fitted with a plunger (5) and comprising a manual, tubular actuation system (7), comprising an output member (9, 19) displaceable in the direction of advance of the plunger (5), an operating head (8) which can be moved axially and rotationally, further a drive element (11) which can rotate relative to the output member (9, 19) seated inside it, and a guide element (24) for the output member (9, 19)

wherein upon axial displacement of the operating head (8) the drive element (11) is displaceable in the direction of advance of the plunger (5) from a rest position into an end position and back and where this motion is transmitted to the output member (9, 19) connected to the drive element (11), wherein for the rest position the output member (9, 19) moved away from the plunger (5) by rotating the operating head (8) can be displaced by the drive element (11) in the direction of advance in relation to a plunger stroke required for the related particular quantity of liquid which must be injected without the output member (9, 19) thereby touching the plunger, and wherein during the transit of the drive element (9, 19) from the rest position to the end position the output member (9, 19) impacts the plunger (5) which is thereby displaced along a pre-set plunger path, characterized in that the drive element (11) is non-rotatably connected to the operating head (8) and both carry out jointly all their motions, the guide element (24) is rigidly affixed to the rear part (3) of the device (1), the output member (9, 19) is non-rotatably supported in the guide element (24), the guide element (24) is in front of the drive element (11) inside the actuation system (7).

2. Device defined in claim 1, characterized in that the drive element (11) is kept in the rest position by a first spring (16) and is displaceable into the end position against the force of this first spring (16).

3. Device defined in claim 1, characterized in that the output member (9, 19) comprises a rod (9) fitted with a front flange and has planar surfaces (12, 12') at two mutually opposite sides and elsewhere threaded circular areas (13, 13').

4. Device defined in claim 1, characterized in that a rotary detent (20) is present between the guide element (24) or parts non-rotatably affixed to it and the drive element (11) or parts non-rotatably affixed to it.

5. Device defined in claim 4, characterized in that the rotary detent (20) is a serrated detent.

6. Device defined in claim 4, characterized in that the parts (21, 22) of the rotary detent (20) are mutually displaceable against springs (16, 35) located either between the nonrotatable parts such as the ampoule holder (29) and the rear part (3) or between rotary parts such as the drive element (11) and the sleeve part (21).

7. Device defined in claim 6, characterized in that the rotational direction of the operating head (8) setting the injection dose is that direction allowing the rotary detent (20) to move with little drag.

8. Device defined in claim 4, characterized in that the rotary detent (20) can be relieved by removing the ampoule (4) from the device (1) in that the ampoule holder (34)—which otherwise presses by means of the spring (35) against the ampoule (4)—is being advanced, whereby the operating head (8) and with it the drive element (11) are rotatable without drag in both directions and the output member (9, 19) thereby is rotatable back into its initial position.

* * * * *